(12) United States Patent
Grela et al.

(10) Patent No.: US 9,610,572 B2
(45) Date of Patent: Apr. 4, 2017

(54) RUTHENIUM COMPLEXES, METHOD OF THEIR PRODUCTION AND THEIR USAGE

(71) Applicant: Apeiron Synthesis Spólka Akcyjna, Wroclaw (PL)

(72) Inventors: Karol Grela, Warsaw (PL); Stefan Czarnocki, Łosice (PL)

(73) Assignee: Apeiron Synthesis Spolka Akcyjna, Wroclaw (PL)

( * ) Notice: Subject to any disclaimer, the term of this patent is extended or adjusted under 35 U.S.C. 154(b) by 0 days.

(21) Appl. No.: 14/443,034

(22) PCT Filed: Nov. 14, 2013

(86) PCT No.: PCT/IB2013/002543
§ 371 (c)(1),
(2) Date: May 14, 2015

(87) PCT Pub. No.: WO2014/076548
PCT Pub. Date: May 22, 2014

(65) Prior Publication Data
US 2015/0329576 A1    Nov. 19, 2015

(30) Foreign Application Priority Data
Nov. 15, 2012    (PL) .......................... 401631

(51) Int. Cl.
| | |
|---|---|
| *C08F 4/80* | (2006.01) |
| *C07F 15/00* | (2006.01) |
| *B01J 31/00* | (2006.01) |
| *C08F 132/08* | (2006.01) |
| *C07C 6/00* | (2006.01) |
| *C07C 6/06* | (2006.01) |
| *C07C 67/333* | (2006.01) |

(52) U.S. Cl.
CPC .................. *B01J 31/00* (2013.01); *C07C 6/00* (2013.01); *C07C 6/06* (2013.01); *C07C 67/333* (2013.01); *C07F 15/0046* (2013.01); *C08F 4/80* (2013.01); *C08F 132/08* (2013.01); *C07C 2101/10* (2013.01); *C07C 2102/22* (2013.01); *C07C 2531/22* (2013.01); *C07C 2531/28* (2013.01)

(58) Field of Classification Search
CPC ............... C07F 15/0046; B01J 31/2278; B01J 31/2273; B01J 31/2269; B01J 31/2265; C08F 4/80
See application file for complete search history.

(56) References Cited

U.S. PATENT DOCUMENTS

| 9,074,028 B2 | 7/2015 | Grela et al. | |
|---|---|---|---|
| 2003/0144437 A1* | 7/2003 | Bell | ...................... B01J 31/2265 526/171 |
| 2012/0101279 A1 | 4/2012 | Winde et al. | |

FOREIGN PATENT DOCUMENTS

| EP | 2 255 877 A1 | 12/2010 | |
|---|---|---|---|
| PL | 395131 A1 | 12/2012 | |
| WO | 2010/096445 A2 | 8/2010 | |
| WO | 2011/079439 A1 | 7/2011 | |
| WO | WO 2011/079439 A1 * | 7/2011 | ........... C07C 217/84 |

OTHER PUBLICATIONS

Slugovc et al. Organometallics 2005, 24, 2255-2258.*
Zukowska et al. Organometallics 2012, 31, 462-469.*
Polish Search Report dated May 21, 2013, for Polish Classification Notification, 1 page.
International Search Report mailed Jan. 31, 2014, for International Application No. PCT/IB2013/002543, 12 pages.
Slugovc et al., "Thermally Switchable Olefin Metathesis Initiators Bearing Chelating Carbenes: Influence of the Chelate's Ring Size," *Organometallics* 24:2255-2258, 2005.
Żukowska et al., "Thermal Switchabilityof N-Chelating Hoveyda-type Catalyst Containing a Secondary Amine Ligand," *Organometallics* 31:462-469, Dec. 13, 2011.
Dragutan et al., "Single-Site Ruthenium Metathesis Catalysts," *Platinum Metals Rev.* 45(4):155-163, 2001.
Monsaert et al., "Latent olefin metathesis catalysts," *Chemical Society Reviews* 38:3360-3372, 2009.
Vougioukalakis et al., "Ruthenium-Based Heterocyclic Carbene-Coordinated Olefin Metathesis Catalysts," *Chem. Rev.* 110:1746-1787, 2010.
Samojlowicz et al., "Ruthenium-Based Olefin Metathesis Catalysts Bearing *N*-Heterocyclic Carbene Ligands," *Chem. Rev.* 109:3708-3742, 2009.
Schuster et al., "Beyond Conventional *N*-Heterocyclic Carbenes: Abnormal, Remote, and Other Classes of NHC Ligands with Reduced Heteroatom Stabilization," *Chem. Rev.* 109:3445-3478, 2009.
Bieniek et al., "Advanced Fine-Tuning of Grubbs/Hoveyda Olefin Metathesis Catalysts: A Further Step toward an Optimum Balance between Antinomic Properties," *J. Am. Chem. Soc.* 128:13652-13653, 2006.

(Continued)

Primary Examiner — Rip A Lee
(74) Attorney, Agent, or Firm — Seed IP Law Group LLP (57) ABSTRACT

The invention concerns the ruthenium complexes of the formula 1:

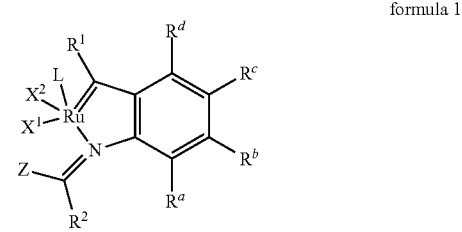

acting as pre(catalysts) in the reaction of metathesis of olefins, as well as a method for their production, and their usage.

10 Claims, 3 Drawing Sheets

(56) References Cited

OTHER PUBLICATIONS

Kozlowska et al., "Chelating Ruthenium Phenolate Complexes: Synthesis, General Catalytic Activity, and Applications in Olefin Metathesis Polymerization," *Chem. Eur. J.* 20:14120-14125, 2014.

* cited by examiner

Fig. 1

Diagram 1. Kinetic profiles of reaction progress with a catalyst of the formula 1a at the temperatures of 40, 80 and 120°C according to Scheme IX

Fig. 2

Diagram 2. Kinetic profiles of reaction progress with a catalyst of the formula 1a in toluene at a temperature of 80°C according to Scheme IX.

Fig. 3

Diagram 3. Kinetic profiles of reaction progress with a catalyst of the formula 1a in mesitylene at a temperature of 120°C according to Scheme IX.

RUTHENIUM COMPLEXES, METHOD OF THEIR PRODUCTION AND THEIR USAGE

FIELD OF THE INVENTION

The invention concerns novel ruthenium complexes, a method of manufacturing thereof, and their usage as pre (catalysts) in the reaction of metathesis of olefins. This invention finds its application in polymerisation of olefins and in broadly understood organic synthesis.

THE STATE OF THE ART

In recent years, a large progress has been achieved in the applications of metathesis of olefin for organic synthesis (Handbook of Metathesis, Volumes I-III: Grubbs, R. H., ed.; Wiley-VCH, 2003; and Michalak, M.; Gulajski, Ł.; Grela, K. "*Alkene Metathesis*" in *Science of Synthesis: Houben-Weyl Methods of Molecular Transformations*, Volume 47a—Alkenes, de Meijere, A., ed.; Georg Thieme Verlag KG, 2010, str. 327-438).

In the state of the art, there are several known carbene complexes of ruthenium that act as (pre)catalysts which possess both a high activity in reactions of metathesis of various kinds, as well as a broad tolerance for functional groups. The above-mentioned combination of properties is necessary for usefulness of such a kind of (pre)catalyst in organic synthesis.

From the practical application point of view, it is very desirable for these ruthenium complexes to be stable for a prolonged period of time at elevated temperature and to be suitable for storing and/or purifying and/or using without any protective-gas atmosphere. It is important in some applications for these catalysts, depending on the reaction conditions, to exhibit the delayed initiation, and to promote the already initiated reaction appropriately fast.

Many ruthenium complexes active in the metathesis of olefins have been studied (see, the review papers: Vougioukalakis, G. C.; Grubbs, R. H. *Chem. Rev.* 2010, 110, 1746; Dragutan, V.; Dragutan, I.; Balaban, A. T. *Platinum Metals Rev.* 2001, 45, 155; Samojlowicz, C.; Bieniek, M.; Grela, K. *Chem. Rev.*, 2009, 109, 3708). Grubbs et al. demonstrated that the benzylidene Ru complexes lacking phosphine ligands, but bearing two pyridine ligands: Gru-III and Gru-III' were characterised by much faster initiation and propagation rate in many metathesis reactions, including the reactions of ring-opening metathetic polymerisation (ROMP). Similarly, the European investigators introduced the indenylidene complex Ind-III having no phosphine ligand but containing one molecule of pyridine as a convenient metathesis catalyst, also exhibiting a high activity in the ROMP polymerisation. The fast-initiating complexes Gru-III, Gru-III' and Ind-III, containing no phosphine ligand in their composition, but containing one or two pyridine molecules, are referred to as III-rd generation catalysts in the literature.

Gru-III

Gru-III'

Ind-III

Mes = 2,3,6-trimethylphenyl

In some applications of metathesis such as mould ROMP polymerisation and other ones, it is preferred to carry out the process in such a manner that the reaction does not start immediately after admixing the substrate and the catalyst, but it starts later, after initiation by chemical agents, temperature, or light. According to the literature reports, HCl is often used as a chemical initiator. The catalysts showing delayed initiation are often termed "dormant catalysts" or "latent catalysts"; see the reviews: Monsaert, S.; Vila, A. L.; Drozdzak, R.; Van Der Voort, P.; Verpoort, F., *Chem. Soc. Rev.*, 2009, 38, 3360; and Szadkowska, A.; Grela, K. *Curr. Org. Chem.*, 2008, 12, 1631. Exemplary catalysts having this feature are the complexes vdShaf, Grubbs-1, Grubbs-2, Grubbs-3, Verport, Slugovc-1:

vdShaaf (L = PCy₃)
Grubbs-1 (L = SIMes)
Verpoort

Slugovc-1
Grubbs-2

Grubbs-3
Piet-1 (L = PCy₃)
Piet-2 (L = SIMes)

Cy₃P =

SIMes =

DISCLOSURE OF THE INVENTION

It was unexpectedly found that novel ruthenium complexes according to the invention, represented by the formula 1:

formula 1 that contain chelate rings formed by an imine nitrogen atom and an oxygen atom, are thermally stable and show a good catalytic activity. The complexes of the formula 1 are stable in an oxygen-containing atmosphere. Moreover, these compounds show a marked change of the catalytic activity with respect to temperature, what may find application for controlling the catalytic processes by changing the temperature of the reaction mixture. Additionally, these compounds show unexpectedly retardation of the catalytic reaction in the presence of hydrogen chloride or trimethylsilyl chloride. Disappearance of the catalytic activity is reversible by removal of the retardant from the reaction medium, e.g., by heating. Such a controlled reversible deactivation of the catalyst under the influence of used additives may find application in controlling the catalytic process of the polymerisation reaction.

The complexes of the formula 1 according to the invention find a wide range of applications. To a good result, one can perform both numerous ring-closing metathesis reactions as well as ring-opening metathetic polymerisations (ROMP).

Thus, the synthesis of compounds containing a carbon-carbon double bond as well as other functional groups, and using novel catalysts according to the invention, are carried out to a very good result.

The invention relates to novel ruthenium complexes, having in their structure a chelating benzylidene ligand containing a coordinate ruthenium-nitrogen bond, of the formula 1:

formula 1 wherein:
L is a neutral ligand;
X and $X^1$ independently represent an anionic ligand;
$R^1$, $R^2$, $R^a$, $R^b$, $R^c$, $R^d$ independently represent a hydrogen atom, a halogen atom, $C_1$-$C_{25}$ alkyl, $C_1$-$C_{25}$ perfluoroalkyl, $C_2$-$C_{25}$ alkene, $C_3$-$C_7$ cycloalkyl, $C_2$-$C_{25}$ alkenyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryl, $C_5$-$C_{20}$ heteroaryl, 3-12-membered heterocyclyl, ether (—OR'), thioether (—SR'), nitro (—NO$_2$), cyano (—CN), carboxy and ester (—COOR'), amido (—CONR'R''), sulphono (—SO$_2$R'), sulphonamido (—SO$_2$NR'R''), formyl and keto (—COR') groups, wherein R' and R'' independently represent a hydrogen atom, $C_1$-$C_5$ alkyl, $C_1$-$C_5$ perfluoroalkyl, $C_5$-$C_{24}$ aryl, $C_5$-$C_{24}$ heteroaryl, $C_5$-$C_{24}$ perfluoroaryl;
Z independently represents heteroaryl $C_5$-$C_{20}$, 3-12-membered heterocyclyl, formyl and keto (—COR$^{Z1}$), carboxy and ester (—COOR$^{Z1}$), thioester (—CSOR$^{Z1}$), nitro (—NO$_2$), amido (—CONR$^{Z1}$R$^{Z''}$), sulphono (—SO$_2$R$^{Z1}$), sulphonamido (—SO$_2$NR$^{Z1}$R$^{Z''}$), —CR$^{Z1}$R$^{Z''}$COR$^{Z1}$, —CR$^{Z1}$R$^{Z''}$COOR$^{Z1}$, —CR$^{Z1}$R$^{Z''}$CONR$^{Z1}$R$^{Z''}$—CR$^{Z1}$R$^{Z''}$SO$_2$R$^{Z1}$, —CR$^{Z1}$R$^{Z''}$SO$_2$NR$^{Z1}$R$^{Z''}$; wherein R$^{Z1}$ and R$^{Z''}$ independently represent a hydrogen atom, $C_1$-$C_5$ alkyl, $C_1$-$C_5$ perfluoroalkyl, $C_5$-$C_{24}$ aryl, $C_5$-$C_{24}$ heteroaryl, $C_5$-$C_{24}$ perfluoroaryl;
the anionic ligands $X^1$, $X^2$ independently represent a halogen atom, —CN, —SCN, —OR$^4$, —SR$^4$, —O(C=O)R$^4$, —O(SO$_2$)R$^4$, —OP(O)R$_2^4$, —OSiR$_3^4$, wherein $R^4$ represents $C_1$-$C_{12}$ alkyl, $C_3$-$C_{12}$ cycloalkyl, $C_2$-$C_{12}$ alkenyl, or $C_5$-$C_{20}$ aryl, being optionally substituted with at least one $C_1$-$C_{12}$ alkyl, $C_1$-$C_{12}$ perhaloalkyl, $C_1$-$C_{12}$ alkoxy or a halogen atom; and also
the neutral ligand L is selected independently from the group comprising so called N-heterocyclic carbene ligands represented by the formula 2a, 2b, 2c, 2d, 2e, 2f, 2g, 2h, 2i, 2j, 2k, 2l, 2m, 2n, 2o or 2p:

formula 2a formula 2b formula 2c formula 2d formula 2e

-continued formula 2f formula 2g formula 2h formula 2i formula 2j formula 2k formula 2l formula 2m formula 2n formula 2o formula 2p wherein:
$R^{60}$, each $R^{50}$, $R^{70}$ and $R^{80}$ independently represents $C_1$-$C_{12}$ alkyl, $C_3$-$C_{12}$ cycloalkyl, $C_2$-$C_{12}$ alkenyl, $C_5$-$C_{20}$ aryl, or $C_5$-$C_{20}$ heteroaryl, being optionally substituted with at least one $C_1$-$C_{12}$ alkyl, $C_1$-$C_{12}$ perhaloalkyl, $C_1$-$C_{12}$ alkoxy or a halogen atom;
each $R^5$, $R^6$, $R^7$, $R^8$, $R^9$ and $R^{10}$ independently represents a hydrogen atom, $C_1$-$C_{12}$ alkyl, $C_3$-$C_{12}$ cycloalkyl, $C_2$-$C_{12}$ alkenyl, $C_5$-$C_{20}$ aryl, or $C_5$-$C_{20}$ heteroaryl, being optionally substituted with at least one $C_1$-$C_{12}$ alkyl, $C_1$-$C_{12}$ perhaloalkyl, $C_1$-$C_{12}$ alkoxy or a halogen atom;
and any substituents selected from the group comprising $R^5$, $R^6$, $R^7$, $R^8$, $R^9$ and $R^{10}$ as well as $R^{50}$, $R^{60}$, $R^{70}$ and $R^{80}$ may optionally bind each other to form a cyclic or macrocyclic system.

Preferably, in the complex of the formula 1, ligand $X^1$ and $X^2$ denote a chlorine atom.

Preferably, in the complex of the formula 1, ligand L denotes a ligand of the formula 2a or 2b:

formula 2a formula 2b wherein the substituents $R^{50}$, $R^{60}$, $R^5$, $R^6$, $R^7$ and $R^8$ are as above defined.

Most preferably, the complex according to the invention is of the formula 1a:

formula 1a

The invention relates also to the process for preparation of the ruthenium complex of the formula 1, in which a compound of the formula 3 formula 3 wherein:
R, $R^1$, $R^2$, $R^a$, $R^b$, $R^c$, $R^d$ and Z are as above defined, and $R^{13}$, $R^{14}$ independently represent a hydrogen atom, a halogen atom, $C_1$-$C_{25}$ alkyl, $C_1$-$C_{25}$ perfluoroalkyl, $C_2$-$C_{25}$ alkene, $C_3$-$C_7$ cycloalkyl, $C_2$-$C_{25}$ alkenyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryl, $C_5$-$C_{20}$ heteroaryl, 3-12-membered heterocyclyl, preferably, a hydrogen atom, nitro (—$NO_2$), cyano (—CN), carboxy and ester (—$COOR^{Xi}$), amido (—$CONR^{Xi}R^{Xii}$), sulphono (—$SO_2R^{Xi}$), sulphonamido (—$SO_2NR^{Xi}R^{Xii}$), formyl and keto (—$COR^{Xi}$), wherein $R^{Xi}$ and $R^{Xii}$ independently represent a hydrogen atom, $C_1$-$C_5$ alkyl, $C_1$-$C_5$ perfluoroalkyl, $C_5$-$C_{24}$ aryl;
reacted with a carbene ruthenium complex of the formula 4a, 4b, 4c or 4d:

formula 4a formula 4b formula 4c formula 4d wherein
$L^1$, $L^2$ and $L^3$ independently represent a neutral ligand;
$X^1$ and $X^2$ independently represent an anionic ligand;
$R^{11}$ is identical to $R^1$ in the formula 1;
$R^{12}$ is a hydrogen atom, $C_5$-$C_{20}$ aryl, $C_5$-$C_{20}$ heteroaryl, vinyl or allenyl,
the reaction being carried out in a period of from 1 min to 250 hrs, at a temperature of from 0 to 150° C., in a protic solvent or in an aprotic, chlorinated solvent, or in an aromatic hydrocarbon solvent, or in a mixture thereof, in the presence of oxygen.

Preferably, the reaction is carried out in a solvent selected from the group comprising methylene chloride, toluene or a mixture thereof.

The invention concerns also the use of a ruthenium complex of the formula 1 as a catalyst in the catalytic metathesis of olefins.

Preferably, the catalysed metathesis comprises a reaction selected from ring-closing metathesis, homometathesis, cross-metathesis, "alkene-alkyne" type metathesis or ring-opening metathetic polymerisation; more preferably, the catalysed metathesis is dicyclopentadiene ring-opening metathetic polymerisation.

Preferably, the catalysed reaction of metathesis of olefins is reversibly retarded by addition of an acid or halogen-derivatives of alkanes and silanes.

The carbene ligands may be coordinated classically as in the structures 2a-2h, or non-classically ("abnormal carbenes," see, Chem. Rev. 2009, 109, 3445), as in the structures 2i-2p.

The process for preparation of the ruthenium complexes according to the invention is shown in Schemes I-IV:

Scheme I

Scheme II wherein R, $R^1$, $R^2$, Z, $R^{13}$, $R^{14}$ are as above defined, with the carbene ruthenium complex of the formula 4a, 4b, 4c or 4d:

as presented in Schemes V-VIII below:

The above process for preparation of the complexes of the formula 1 according to the invention is novel and unexpected, since there is an exchange of styrene in the first step of the reaction, and the reaction of oxidation of the C—N bond to C═N occurs unexpectedly under the influence of oxygen in the next step.

Alternatively, a compound of the formula 1 may be prepared by reacting the compound of the formula 5

Scheme VI

Scheme VII

Scheme VIII

The term "a halogen atom," as used herein, denotes an atom of an element selected from F, Cl, Br, I.

The term "carbene" denotes a moiety containing a neutral carbon atom having the valence number equal to two, and two unpaired valence electrons. The term "carbene" comprises also carbene analogues in which the carbon atom is replaced with another chemical element such as boron, silicon, germanium, tin, lead, nitrogen, phosphorus, sulphur, selenium, and tellurium.

The term "alkyl" relates to a saturated, linear or branched hydrocarbon substituent having the indicated number of carbon atoms. Examples of an alkyl substituent are methyl, ethyl, n-propyl, n-butyl, n-pentyl, n-hexyl, n-heptyl, n-octyl, n-nonyl, and n-decyl. The representative $(C_1-C_{10})$alkyls comprise isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl, and the like.

The term "alkoxy" relates to an alkyl substituent, as above defined, linked via an oxygen atom.

The term "perfluoroalkyl" denotes alkyl, as above defined, in which all hydrogen atoms have been replaced with identical or different halogen atoms.

The term "cycloalkyl" relates to a saturated mono- or polycyclic hydrocarbon substituent having the indicated number of carbon atoms. The examples of a cycloalkyl substituent are cyclopropyl, cyclobutyl, cyclopentyl, cyclohexyl, cycloheptyl, cyclooctyl, cyclononyl, cyclodecyl, and the like.

The term "alkenyl" relates to an unsaturated, linear, or branched acyclic hydrocarbon substituent having the indicated number of carbon atoms and containing at least one carbon-carbon double bond. The examples of an alkenyl substituent are vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl, and the like.

The term "cycloalkenyl" relates to an unsaturated mono- or polycyclic hydrocarbon substituent having the indicated number of carbon atoms and containing at least one carbon-carbon double bond. The examples of a cycloalkenyl substituent are cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodekadienyl, and the like.

The term "alkynyl" relates to an unsaturated, linear, or branched acyclic hydrocarbon substituent having the indicated number of carbon atoms and containing at least one carbon-carbon triple bond. The examples of an alkynyl substituent are acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, and the like.

The term "cycloalkynyl" relates to an unsaturated mono- or polycyclic hydrocarbon substituent having the indicated number of carbon atoms and containing at least one carbon-carbon triple bond. The examples of a cycloalkynyl substituent are cyclohexynyl, cycloheptynyl, cyclooctynyl, and the like.

The term "aryl" relates to an aromatic mono- or polycyclic hydrocarbon substituent having the indicated number of carbon atoms. The examples of an aryl substituent are phenyl, tolyl, xylyl, naphthyl, and the like.

The term "heteroaryl" relates to an aromatic mono- or polycyclic hydrocarbon substituent having the indicated number of carbon atoms, in which at least one carbon atom has been replaced with a heteroatom selected from O, N and S. The examples of a heteroaryl substituent are furyl, thienyl, imidazolyl, oxazolyl, thiazolyl, isoxazolyl, triazolyl, oxadiazolyl, tiadiazolyl, tetrazolyl, pyridyl, pyrimidyl, triazinyl, indolyl, benzo[b]furyl, benzo[b]thienyl, indazolyl, benzimidazolyl, azaindolyl, quinolyl, isoquinolyl, carbazolyl, and the like.

The term "heterocyclyl" relates to a saturated or partially unsaturated, mono- or polycyclic hydrocarbon substituent, having the indicated number of carbon atoms, in which at least one carbon atom has been replaced with a heteroatom selected from O, N and S. The examples of a heterocyclic substituent are furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl, quinolinyl, isoquinolinyl, chromonyl, coumarinyl, indolyl, indolizinyl, benzo[b]furanyl, benzo[b]thiophenyl, indazolyl, purinyl, 4H-quinolizinyl, isoquinolyl, quinolyl, phthalazinyl, naphthyridinyl, carbazolyl, β-carbolinyl, and the like.

The term "a neutral ligand" relates to a substituent having no charge, capable for coordination with a metallic centre (a ruthenium atom). The examples of such ligands may be amines, phosphines and oxides thereof, alkyl and aryl phosphites and phosphates, arsines and oxides thereof, ethers, alkyl and aryl sulphides, coordinated hydrocarbons, alkyl and aryl halogenides.

The term "indenylene" relates to an unsaturated hydrocarbon substituent having an indene structure (benzocyclopentadiene).

The term "heteroindenylene" relates to an indenylene substituent, as above defined, in which at least one carbon atom has been replaced with a heteroatom selected from the group comprising nitrogen, oxygen, sulphur.

The term "an anionic ligand" relates to a substituent capable for coordination with a metallic centre (a ruthenium atom), having a charge capable for partial or complete compensation of the charge of the metallic centre. The examples of such ligands may be: fluoride, chloride, bromide, iodide, cyanide, cyanate and thiocyanate anions, anions of carboxylic acids, anions of alcohols, anions of phenols, anions of thiols and thiophenols, anions of hydrocarbons having a delocalised charge (eg. cyclopentadiene), anions of (organo)sulphuric and (organo)phosphoric acids, as well as of esters thereof (such as, eg., anions of alkylsulphonic and arylsulphonic acids, anions of alkylphosphoric and arylphosphoric acids, anions of alkyl and aryl esters of sulphuric acid, anions of alkyl and aryl esters of phosphoric acids, anions of alkyl and aryl esters of alkylphosphoric and arylphosphoric acids). Optionally, the anion ligand may have the groups $L^1$, $L^2$, $L^3$ linked like the catechol anion, acetylacetone anion, salicylaldehyde anion. The anionic ligands ($X^1$, $X^2$) as well as the neutral ligands ($L^1$, $L^2$, $L^3$) may be linked together, to form the multidentate ligands, for example: a bidentate ligand a tridentate ligand a tetradentate ligand a bidentate ligand a tridentate ligand a tetradentate ligand a bidentate ligand a tridentate ligand

The examples of such ligands are: catechol anion, acetylacetone anion, as well as salicylaldehyde anion.

The term "chlorinated solvent" denotes an organic solvent containing in its molecule structure at least one atom from the list comprising: fluorine, chlorine, bromine and iodine; more preferably, more than one halogen atom. The examples of such solvents are: dichloromethane, tetrachloromethane (carbon tetrachloride), chloroform, 1,2-dichloroethane, chlorobenzene, perfluorotoluene, freons and others.

The term "the halogen derivatives of alkanes and silanes" relates to alkanes and silanes containing in their structures at least one atom selected from the list comprising: fluorine, chlorine, bromine and iodine; preferably, more than one. The examples of such derivatives are tetrachloromethane (carbon tetrachloride), trichloromethane, hexachloroethylene ($C_2Cl_6$), tetrabromosilane ($SiBr_4$), phenyltrichlorosilane, chlorotrimethylsilane.

BRIEF DESCRIPTION OF FIGURES OF DRAWINGS

For better understanding, the invention has been illustrated in examples of embodiment as well as in enclosed figures of drawings, of which.

METHODS OF PUTTING THE INVENTION INTO PRACTICE

The following examples explain preparation and use of novel ruthenium complexes according to the invention.

EXAMPLES

Example I

Synthesis of the Catalyst of the Formula 1a formula 1a

Procedure A (according to Scheme I): Using the protective argon atmosphere, the Schlenk vessel was charged with anhydrous CuCl (0.0198 g, 0.2 mmol, 2 equivalents), the compound of the formula 3:

formula 3

(0.0246 g, 0.12 mmol, 1.2 equivalent), dry, deoxygenated toluene (4 ml) as well as a solid carbene complex of the metal of the formula 4c, wherein $X^1$ and $X^2$ denote chlorine, $L^1$ denotes tricyclohexylphosphine ($PCy_3$), $L^2$ denotes an NHC ligand of the formula 2a, wherein $R^{50}$ and $R^{60}$ denote 2,4,6-trimethylphenyl, $R^5$, $R^6$, $R^7$ and $R^8$ denote a hydrogen atom; and $R^{12}$ denotes phenyl (complex Ind-II, 0.0949 g, 0.1 mmol). The obtained suspension was stirred at a temperature of 60° C. for 30 min. The protective argon atmosphere was replaced with air and warming at a temperature of 60° C. was continued for 30 min. The reaction mixture was chromatographed over silica gel, using 40% ethyl acetate in cyclohexane as an eluent. Then the product-containing fractions were combined, the solvents were distilled of on a rotary evaporator, leaving the catalyst of the formula 1a as a red solid (0.042 g, 64%).

Procedure B (according to Scheme II): Using the protective argon atmosphere, the Schlenk vessel was charged with the styrene derivative 3 (0.0246 g, 0.12 mmol, 1.2 equivalent), dry, deoxygenated toluene (4 ml) as well as the solid carbene complex of the metal of the formula 4d, wherein $X^1$ and $X^2$ denote chlorine, $L^1$ denotes pyridine, $L^2$ denotes an NHC ligand of the formula 2a, wherein $R^{50}$ and $R^{60}$ denote 2,4,6-trimethylphenyl, $R^5$, $R^6$, $R^7$ and $R^8$ denote a hydrogen atom; and $R^{12}$ denotes phenyl (complex Ind-III, 0.0784 g, 0.1 mmol). The obtained suspension was stirred at a temperature of 80° C. for 15 min. The protective argon atmosphere was replaced with air and warming at a temperature of 80° C. for 20 min. The reaction mixture was chromatographed over silica gel, using 40% ethyl acetate in cyclohexane as an eluent. Then the product-containing fractions were combined, the solvents were distilled of on a rotary evaporator, to yield the catalyst of the formula 1a as a red solid (0.026 g, 40%).

$^1$H NMR (500 MHz, $CD_2Cl_2$): 16.95 (s, 1H, Ru=CHAr), 8.98 (s, 1H, N=CHCOOMe), 7.57-7.54 (m, 1H), 7.40 (d, J=8 Hz, 1H), 7.32-7.29 (m, 1H), 7.05 (bs, 4H, $CH_2CH_2$), 6.98-6.96 (m, 1H), 4.07 (s, 4H), 3.62 (s, 3H, $CH_3O$), 2.50 (bs, 12H), 2.39 (bs, 6H).

$^{13}$C NMR (125 MHz, $CD_2Cl_2$): 304.5 (Ru=CH), 208.7 (RuCNN), 169.3, 159.1, 141.9, 139.7, 138.7, 134.8, 129.5, 127.9, 121.5, 117.2, 54.4, 52.2, 21.2, 19.2.

HR MS (ESI) Calculated for: $C_{31}H_{35}N_3O_2NaCl_2Ru$ ([M+Na]$^+$) m/z: 676.1048.
Found: 676.1057.

X-Ray structural analysis for the compound 1a:

The examples of uses of the compound 1a as a catalyst in the ring-closure metathesis reaction as well as in the ROMP polymerisation are shown below.

Example II

Studies on Catalytic Activity in Cyclisation of Diethyl Diallylmalonate

Scheme IX

Procedure A: The Schlenk vessel was charged with a solution of the diene S1 (96.1 mg, 0.4 mmol) in DCM (4 ml), followed by the catalyst 1a (2.61 mg, 1 mol %). The content of the vessel was stirred at a temperature of 40° C. under argon atmosphere. The crude reaction mixture was analysed using a gas chromatograph.

Procedure B: The Schlenk vessel was charged with a solution of the diene S1 (96.1 mg, 0.4 mmol) in toluene (4 ml), followed by the catalyst 1a (2.61 mg, 1 mol %). The content of the vessel was stirred at a temperature of 80° C. under argon atmosphere. The crude reaction mixture was analysed using a gas chromatograph.

Procedure C: The Schlenk vessel was charged with a solution of the diene S1 (96.1 mg, 0.4 mmol) in toluene (4 ml), to which was added a solution of HCl in dioxane (50 μL, 50 mol %), followed by the catalyst 1a (2.61 mg, 1 mol %). The content of the vessel was stirred at a temperature of 80° C. under argon atmosphere. The crude reaction mixture was analysed using a gas chromatograph.

Procedure D: The Schlenk vessel was charged with a solution of the diene S1 (96.1 mg, 0.4 mmol) in toluene (4 ml), to which was added chlorotrimethylsilane (3.46 μL, 10 mol %), followed by the catalyst 1a (2.61 mg, 1 mol %). The content of the vessel was stirred at a temperature of 80° C. under argon atmosphere. The crude reaction mixture was analysed using a gas chromatograph.

Procedure E: The Schlenk vessel was charged with a solution of the diene S1 (96.1 mg, 0.4 mmol) in mesitylene (4 ml), followed by the catalyst 1a (2.61 mg, 1 mol %). The content of the vessel was stirred at a temperature of 120° C. under argon atmosphere. The crude reaction mixture was analysed using a gas chromatograph.

Procedure F: The Schlenk vessel was charged with a solution of the diene S1 (96.1 mg, 0.4 mmol) in mesitylene (4 ml), to which was added a solution of HCl in dioxane (50 μL, 50 mol %), followed by the catalyst 1a (2.61 mg, 1 mol %). The content of the vessel was stirred at a temperature of 120° C. under argon atmosphere. The crude reaction mixture was analysed using a gas chromatograph.

Procedure G: The Schlenk vessel was charged with a solution of the diene S1 (96.1 mg, 0.4 mmol) in mesitylene (4 ml), to which was added chlorotrimethylsilane (3.46 μL, 10 mol %), followed by the catalyst 1a (2.61 mg, 1 mol %). The content of the vessel was stirred at a temperature of 120° C. under argon atmosphere. The crude reaction mixture was analysed using a gas chromatograph.

Figure 1:
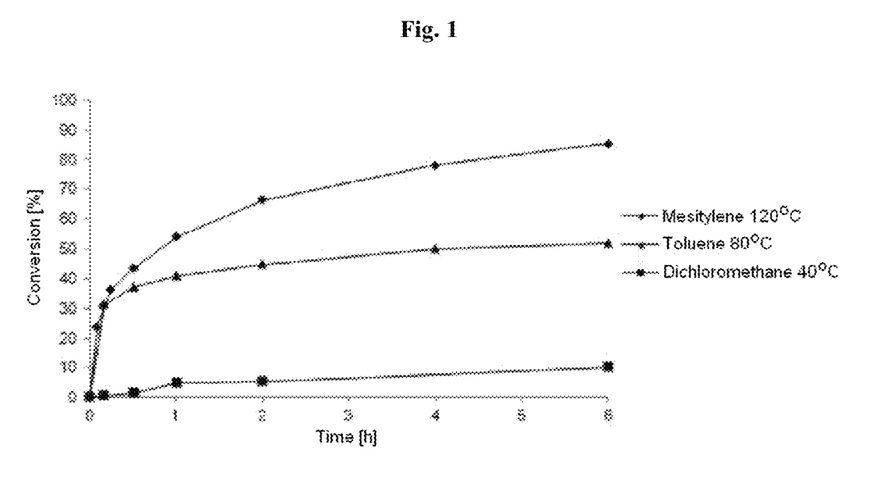
FIG. 1 presents Diagram 1—Kinetic profiles of the reaction progress with a catalyst of the formula 1a at the temperatures of 40, 80 and 120° C. according to Scheme IX
Figure 2:
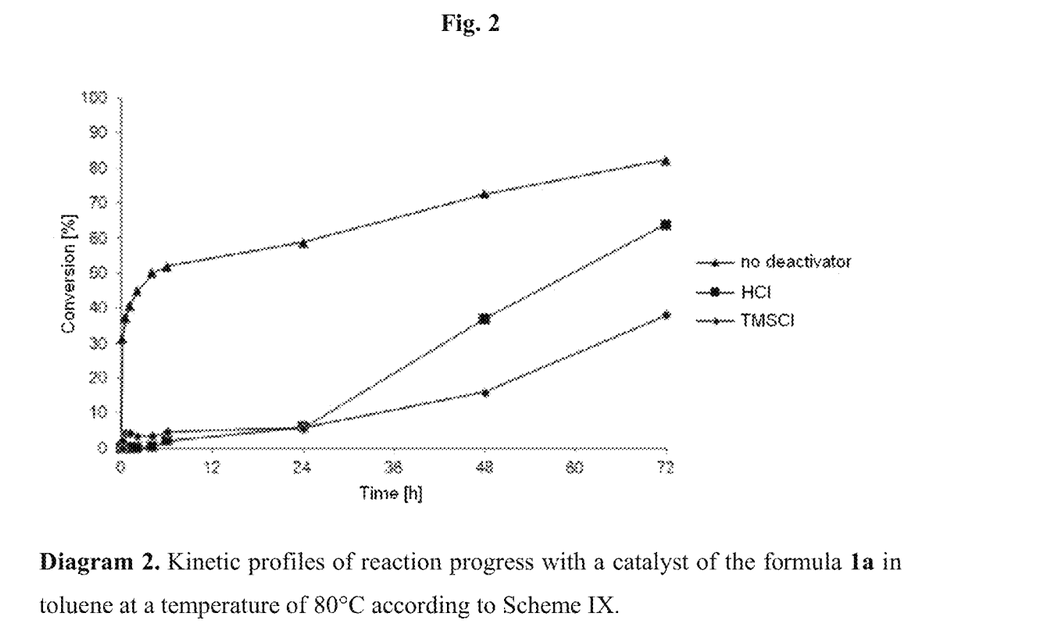
FIG. 2 presents Diagram 2—Kinetic profiles of the reaction progress with a catalyst of the formula 1a in toluene at a temperature of 80° C. according to Scheme IX.
Figure 3:
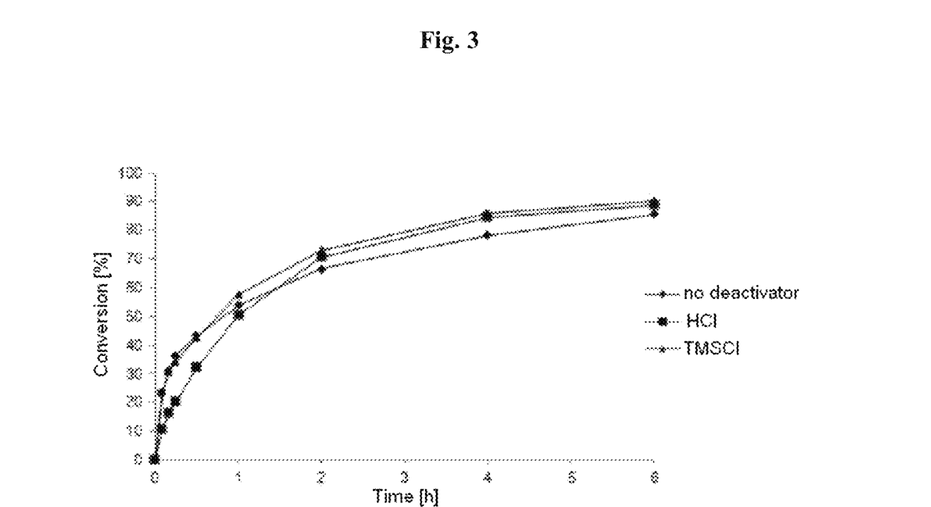
FIG. 3 presents Diagram 3—Kinetic profiles of the reaction progress with a catalyst of the formula 1a in mesitylene at a temperature of 120° C. according to Scheme IX.

The results are shown in diagrams 1-3 presented in FIGS. 1-3, respectively: Diagram 1 (FIG. 1), Diagram 2 (FIG. 2), Diagram 3 (FIG. 3).

The presented results demonstrate that the complexes according to the invention are characterised by a good catalytic activity in the reaction of metathesis of olefins, and they are stable at elevated temperatures.

Additionally, it was shown that addition of HCl or TMSCl resulted in a significant drop of catalytic activity of the complexes according to the invention. Removal of HCl or TMSCl from the reaction medium by heating resulted in recovering the initial catalytic activity of the complexes according to the invention.

Example III

Studies on Catalytic Activity in Polymerisation of Dicyclopentadiene

Scheme X

Procedure A: Under oxygen-containing atmosphere, the polymerisation vial was charged with dicyclopentadiene S2 (1 ml, 7.46 mmol), which after melting was stirred at a temperature of 30° C. Then the catalyst 1a (4.88 mg, 0.1 mol %) in DCM (0.1 ml) was added, and the open vial was heated under oxygen-containing atmosphere at a temperature of 60° C. for 15 min. A hard polymer was obtained.

Procedure B: Under oxygen-containing atmosphere, the polymerisation vial was charged with dicyclopentadiene S2 (1 ml, 7.46 mmol), which after melting was stirred at a temperature of 30° C. Then the catalyst 1a (0.488 mg, 0.01 mol %) in DCM (0.1 ml) was added, and the open vial was heated under oxygen-containing atmosphere at a temperature of 60° C. for 15 min. A hard polymer was obtained.

Procedure C: Under oxygen-containing atmosphere, the polymerisation vial was charged with dicyclopentadiene S2 (1 ml, 7.46 mmol), which after melting was stirred at a temperature of 30° C. Then chlorotrimethylsilane (0.65 μl, 0.1 mol %) and the catalyst 1a (0.488 mg, 0.01 mol %) solution in DCM (0.1 ml) was added, and the vial content was left at a room temperature for 4 days. After this time, no polymer formation was observed. Then the solution was heated at a temperature of 150° C. in the open vial under oxygen-containing atmosphere for 15 min. A hard polymer was obtained.

The above-presented examples of polymerisation reactions indicated that the compounds according to the invention are characterised by a good catalytic activity in the polymerisation reaction. Additionally, it is shown that the polymerisation process may be reversibly retarded by using chlorotrimethylsilane. This process is not known in the literature.

The invention claimed is:
1. A ruthenium complex of formula 1:

formula 1 wherein:
L is a neutral ligand;
$X^1$ and $X^2$ independently represent an anionic ligand;
$R^1$, $R^2$, $R^a$, $R^b$, $R^c$, $R^d$ independently represent a hydrogen atom, a halogen atom, $C_1$-$C_{25}$ alkyl, $C_1$-$C_{25}$ perfluoroalkyl, $C_2$-$C_{25}$ alkene, $C_3$-$C_7$ cycloalkyl, $C_2$-$C_{25}$ alkenyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryl, $C_5$-$C_{20}$ heteroaryl, 3-12-membered heterocyclyl, ether (—OR'), thioether (—SR'), nitro (—NO$_2$), cyano (—CN), carboxy and ester (—COOR'), amido (—CONR'R"), sulphono (—SO$_2$R'), sulphonamido (—SO$_2$NR'R"), formyl or keto (—COR'), wherein R' and R" independently represent a hydrogen atom, $C_1$-$C_5$ alkyl, $C_1$-$C_5$ perfluoroalkyl, $C_5$-$C_{24}$ aryl, $C_5$-$C_{24}$ heteroaryl, or $C_5$-$C_{24}$ perfluoroaryl;
Z independently represents formyl and keto (—COR$^{Z'}$), carboxy and ester (—COOR$^{Z'}$), thioester (—CSOR$^{Z'}$), or amido (—CONR$^{Z'}$R$^{Z''}$), wherein R$^{Z'}$ and R$^{Z''}$ independently represent a hydrogen atom, $C_1$-$C_5$ alkyl, $C_1$-$C_5$ perfluoroalkyl, $C_5$-$C_{24}$ aryl, $C_5$-$C_{24}$ heteroaryl, or $C_5$-$C_{24}$ perfluoroaryl;
the anionic ligands $X^1$, $X^2$ independently represent a halogen atom, —CN, —SCN, —OR$^4$, —SR$^4$, —O(C=O)R$^4$, —O(SO$_2$)R$^4$, —OP(O)R$_2^4$, or —OSiR$_3^4$, where R$^4$ is $C_1$-$C_{12}$ alkyl, $C_3$-$C_{12}$ cycloalkyl, $C_2$-$C_{12}$ alkenyl, or $C_5$-$C_{20}$ aryl, being optionally substituted with at least one $C_1$-$C_{12}$ alkyl, $C_1$-$C_{12}$ perhaloalkyl, $C_1$-$C_{12}$ alkoxy or a halogen atom; and
the neutral ligand L is a N-heterocyclic carbene ligand selected independently from the group consisting of formula 2a, 2b, 2f, and 2g:

formula 2a formula 2b formula 2f

-continued formula 2g wherein:

each $R^{50}$, and $R^{60}$ independently represents $C_1$-$C_{12}$ alkyl, $C_3$-$C_{12}$ cycloalkyl, $C_2$-$C_{12}$ alkenyl, $C_5$-$C_{20}$ aryl, or $C_5$-$C_{20}$ heteroaryl, being optionally substituted with at least one $C_1$-$C_{12}$ alkyl, $C_1$-$C_{12}$ perhaloalkyl, $C_1$-$C_{12}$ alkoxy or a halogen atom;

each $R^5$, $R^6$, $R^7$, $R^8$, $R^9$ and $R^{10}$ independently represents a hydrogen atom, $C_1$-$C_{12}$ alkyl, $C_3$-$C_{12}$ cycloalkyl, $C_2$-$C_{12}$ alkenyl, $C_5$-$C_{20}$ aryl, or $C_5$-$C_{20}$ heteroaryl, being optionally substituted with at least one $C_1$-$C_{12}$ alkyl, $C_1$-$C_{12}$ perhaloalkyl, $C_1$-$C_{12}$ alkoxy or a halogen atom;

and wherein $R^5$, $R^6$, $R^7$, $R^8$, $R^9$, $R^{50}$, and $R^{60}$, may optionally bind each other to form a cyclic or macrocyclic system.

2. The complex according to claim 1, wherein the ligands $X^1$ and $X^2$ denote a chlorine atom.

3. The complex according to claim 1, wherein the neutral ligand L denotes a ligand of formula 2a or 2b:

formula 2a formula 2b wherein the substituents $R^{50}$, $R^{60}$, $R^5$, $R^6$, $R^7$ and $R^8$ are as above defined.

4. A ruthenium complex being represented by formula 1a:

formula 1a

5. A process for preparation of the ruthenium complex as defined in claim 1, comprising:

reacting a compound of formula 3 formula 3 wherein:

R, $R^1$, $R^2$, $R^a$, $R^b$, $R^c$, $R^d$ and Z are as above defined, and $R^{13}$, $R^{14}$ independently represent a hydrogen atom, a halogen atom, $C_1$-$C_{25}$ alkyl, $C_1$-$C_{25}$ perfluoroalkyl, $C_2$-$C_{25}$ alkene, $C_3$-$C_7$ cycloalkyl, $C_2$-$C_{25}$ alkenyl, $C_3$-$C_{25}$ cycloalkenyl, $C_2$-$C_{25}$ alkynyl, $C_3$-$C_{25}$ cycloalkynyl, $C_1$-$C_{25}$ alkoxy, $C_5$-$C_{24}$ aryl, $C_5$-$C_{20}$ heteroaryl, 3-12-membered heterocyclyl, preferably, a hydrogen atom, nitro (—$NO_2$), cyano (—CN), carboxy or ester (—$COOR^{X'}$), amido (—$CONR^{X'}R^{X''}$), sulphono (—$SO_2R^{X'}$), sulphonamido (—$SO_2NR^{X'}R^{X''}$), formyl or keto (—$COR^{X'}$), wherein $R^{X'}$ and $R^{X''}$ independently represent a hydrogen atom, $C_1$-$C_5$ alkyl, $C_1$-$C_5$ perfluoroalkyl, or $C_5$-$C_{24}$ aryl;

with a carbene ruthenium complex of formula 4a, 4b, 4c or 4d:

formula 4a formula 4b formula 4c formula 4d wherein:

$L^1$, $L^2$ and $L^3$ independently represent a neutral ligand;
$X^1$ and $X^2$ independently represent an anionic ligand;
$R^{11}$ is identical to $R^1$ in formula 1;
$R^{12}$ is a hydrogen atom, $C_5$-$C_{20}$ aryl, $C_5$-$C_{20}$ heteroaryl, vinyl or allenyl, wherein, the reaction is carried out in a period of from 1 min to 250 hrs, at a temperature of from 0 to 150° C., in a protic solvent or in an aprotic, chlorinated solvent or in an aromatic hydrocarbon solvent or in a mixture thereof, in the presence of oxygen.

6. The process according to claim 5, wherein the reaction is carried out in a solvent selected from the group comprising methylene chloride, toluene or a mixture thereof.

7. A process of using the ruthenium complex as claimed in claim 1 as a catalyst in the metathesis of olefins, comprising contacting the complex of formula (I) with an olefin.

8. The process according to claim 7, wherein the catalysed metathesis of olefins comprises a reaction selected from ring-closing metathesis, homometathesis, cross-metathesis, "alkene-alkyne" type metathesis or ring-opening metathetic polymerisation.

9. The process according to claim 8, wherein the catalysed metathesis is the ring-opening metathetic polymerisation of dicyclopentadiene.

10. The process of claim 7 wherein the catalysed reaction of metathesis of olefins is reversibly retarded by addition of an acid or halogen derivatives of alkanes and silanes.

* * * * *